US006982167B2

(12) United States Patent
Hahn et al.

(10) Patent No.: US 6,982,167 B2
(45) Date of Patent: Jan. 3, 2006

(54) APPARATUS FOR MAKING A FOLIAR LIQUID

(76) Inventors: George E. Hahn, 205 Liszt Ave., Cardiff by the Sea, CA (US) 92007; Carole Eddington, 1712 Tripp Ct., Las Vegas, NV (US) 89108; James Eddington, 1712 Tripp Ct., Las Vegas, NV (US) 89108

( * ) Notice: Subject to any disclaimer, the term of this patent is extended or adjusted under 35 U.S.C. 154(b) by 503 days.

(21) Appl. No.: 10/299,350

(22) Filed: Nov. 19, 2002

(65) Prior Publication Data

US 2004/0096963 A1 May 20, 2004

(51) Int. Cl.
*C12M 1/00* (2006.01)

(52) U.S. Cl. ................................ 435/289.1; 435/290.4; 435/297.1

(58) Field of Classification Search .............. 435/289.1, 435/290.4, 297.1
See application file for complete search history.

(56) References Cited

U.S. PATENT DOCUMENTS 5,171,687 A * 12/1992 Moller et al. ............ 435/309.1
6,649,405 B2 * 11/2003 Alms et al. .............. 435/296.1
2002/0108498 A1 * 8/2002 Huhn .......................... 99/279
2003/0113908 A1 * 6/2003 Hussey et al. ........... 435/296.1
2004/0032032 A1 * 2/2004 Erickson ...................... 261/93

* cited by examiner

*Primary Examiner*—David A. Redding
(74) *Attorney, Agent, or Firm*—Don E. Erickson

(57) ABSTRACT

The present invention describes all apparatus for making a foliar spray from a liquid and a particulate matter. The apparatus consists of a non-porous liquid receptacle, a basket for holding the particulate matter, intake means for transporting air from a blower to a manifold means for aerating the liquid and the particulate matter, and a blower for supplying the air. The liquid receptacle is typically a substantially horizontal, rectangular tank having a flat bottom and the manifold means includes a selected number of diffuser arms, the number of diffuser arms selected to cover a substantial portion of the area of the bottom surface of the liquid receptacle and is selectively proportionate to the volume of the receptacle. The manifold means may be easily removed from the liquid receptacle by means of a quick-disconnect coupler for ease of cleaning the liquid receptacle once the foliar liquid is removed from the liquid receptacle via outlet means.

35 Claims, 5 Drawing Sheets

APPARATUS FOR MAKING A FOLIAR LIQUID

BACKGROUND OF INVENTION

1. Field of the Invention

Herein described is an apparatus utilizing aerating means for making a foliar liquid from particulate matter having beneficial micro-organisms for use as a foliar spray, a soil drench, and in watering systems as an injectable liquid.

2. Description of the Related Art

Compost tea is a highly concentrated microbial solution produced by extracting beneficial microbes from vermicompost and/or compost. This "tea" is produced by adding nutrients to water that is highly aerated. Compost and/or vermi-compost is then placed in a "tea bag or basket" and suspended in solution and the extraction process begins. Apparatus for making such compost teas are currently being sold, however, the design, while being easy to use in small apparatus, does not scale up to provide an easy to use apparatus for industrial sized, or volume, applications. Notably, the apparatus typically employs an enclosed vertical, cylindrical vat, with the aerating unit suspended from the top of the vat, or the apparatus is suspended in air, and the aerating unit is mounted on the bottom of the unit, and extends vertically in the vat. One of ordinary skill in the art would know that as vermicompost and/or compost is aerated, partially separated material will drop from the basket, and fall to the bottom of the vat. In the vertical, cylindrical vat, this partially separated material will then accumulate at the bottom, and much of the beneficial microbes will remain in the compost. Thus, this design is not efficient.

In addition, this typical design poses a significant problem when cleaning of the vat is required, which is frequent. Cleaning being required alter every brewing cycle. Since the vat must be frequently cleaned in order that the compost tea is not contaminated, anid because the sides and bottom of the vat must be thoroughly washed, a vat design must enable a last and convenient access to the interior of the vat. In the cylindrical vat design, entry to the vat from the top is difficult, and, on large volume applications, frequently the person cleaning the vat must completely enter the vat through a manhole, which may require the use of breathing equipment and protective clothing.

The apparatus of the invention overcomes these problems by describing an apparatus that is easily accessible, and that provide optimal aeration for the volume of liquid being treated.

BRIEF SUMMARY OF THE INVENTION

Described herein is an apparatus for making a foliar spray, soil drench, and watering system injectable liquid. The apparatus Consists of a liquid receptacle, or tank, having a selected volume for receiving a selected amount of liquid, at least one particulate means for receiving a selected amount of particulate matter having beneficial micro-organisms, means for aerating the liquid and the particulate matter, the aerating means being selectively proportionate to the volume of the receptacle/tank. As air is diffused through the liquid receptacle/tank and the particulate matter, the micro-organisms are separated from the particulate material in a manner to be suspended in the liquid. When the brewing cycle is completed, the lid of the liquid receptacle is easily removed. The aerating means, having been installed utilizing quick-disconnect couplers, can be easily removed From the receptacle, providing unobstructed, easy access to the entire surface of the receptacle. The aerating means is comprised of a manifold and diffuser system that may also be easily cleaned outside the apparatus, and then easily reinstalled. The apparatus also includes temperature control means for maintaining the temperature with the liquid receptacle at a selected temperature.

DRAWINGS

FIG. 4 is a partial, perspective view of the

Figure 5:
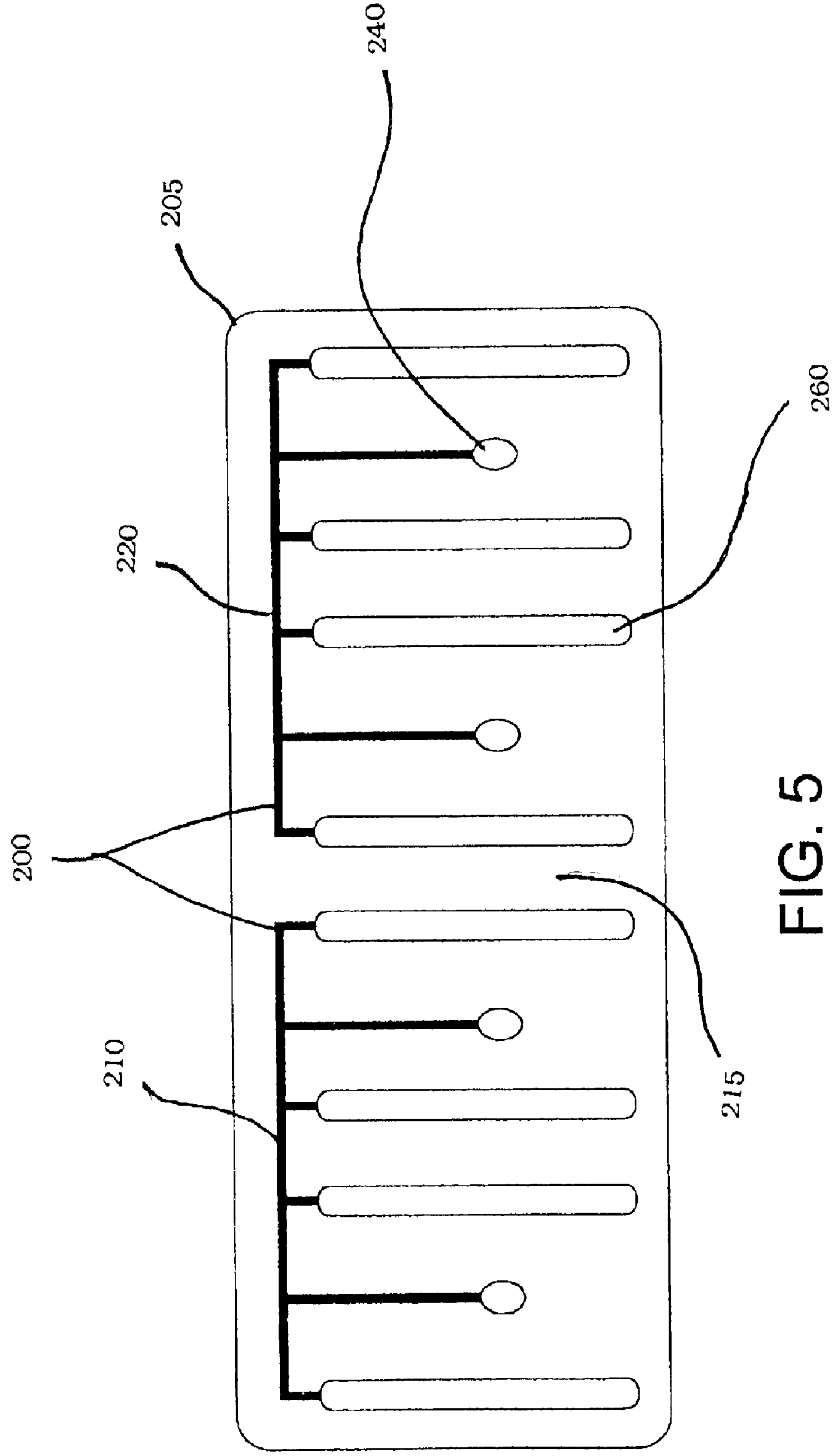

FIG. 5 in a schematic of a second embodiment of the manifold system of the invention.

DETAILED DESCRIPTION OF THE INVENTION

Figure 1:
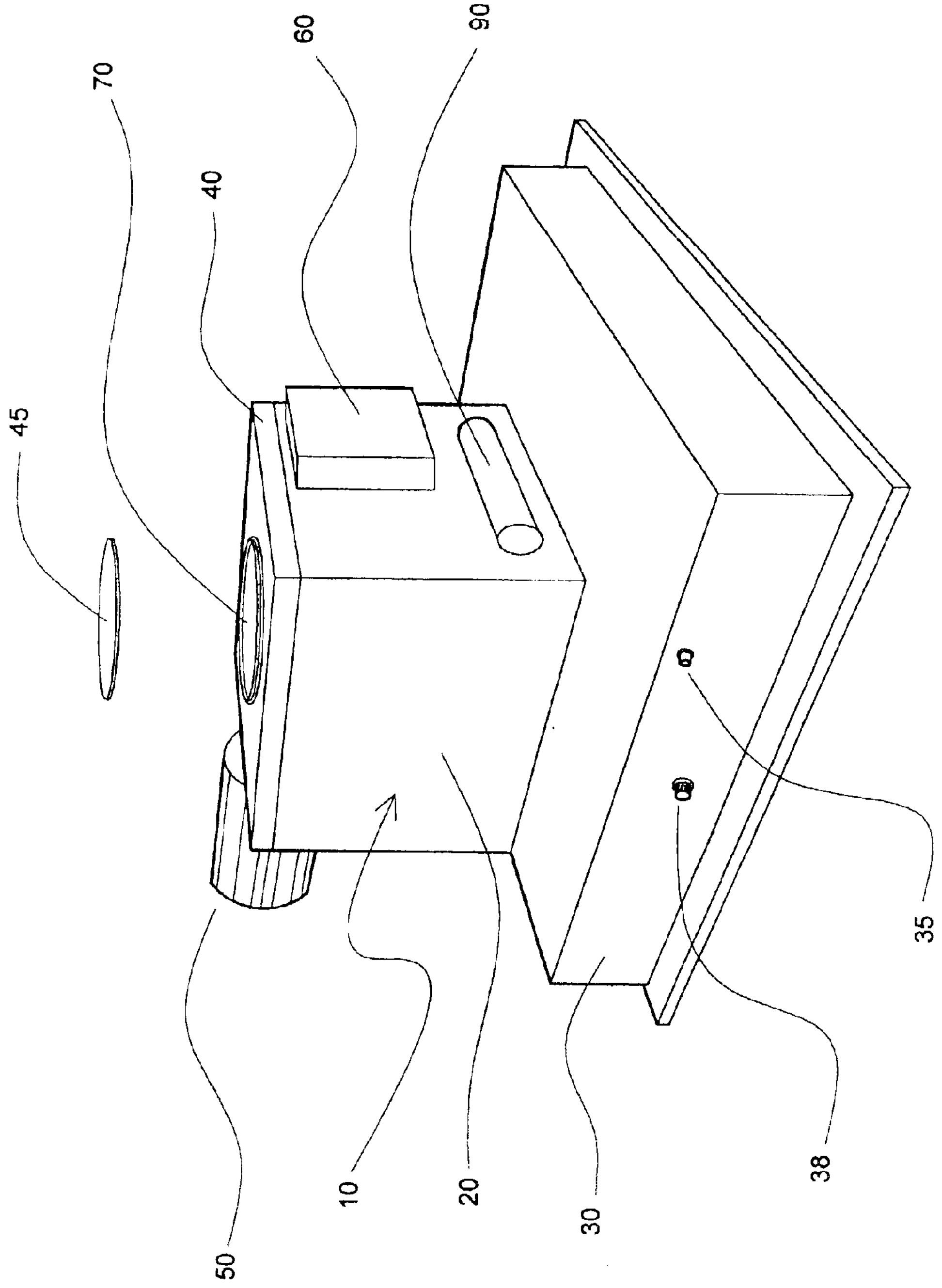
FIG. 1 is a perspective view of the apparatus of the invention.

FIG. 1, describes an apparatus 10 for making a foliar spray having a liquid receptacle 20, a base 30, a lid 40. The base 30 also includes tap drain 35 and exhaust drain 38. Mounted on one side of liquid receptacle 20 is blower 50, for injecting air to an aeration means 100 (not shown), and on the other side is a control means 60, for controlling the duration of aeration and temperature of the liquid in liquid receptacle 20.

The dimensions of the liquid receptacle 20 are selected to receive a selected amount of liquid, which in some instances would be reverse osmosis treated water. Reverse osmosis treated water is used when the foliar spray is to contain beneficial organisms, such as the chitinase producing micro-organisms from worm castings. Impurities in regular water may be detrimental to the life of such microorganisms. In this exemplary embodiment, a 100 gallon liquid receptacle is described, having a width of approximately 30 inches, a length of approximately 31 inches, and a height of approximately 30 inches. This low height enables easy access to the side walls and bottom of the receptacle for cleaning.

Figure 3:
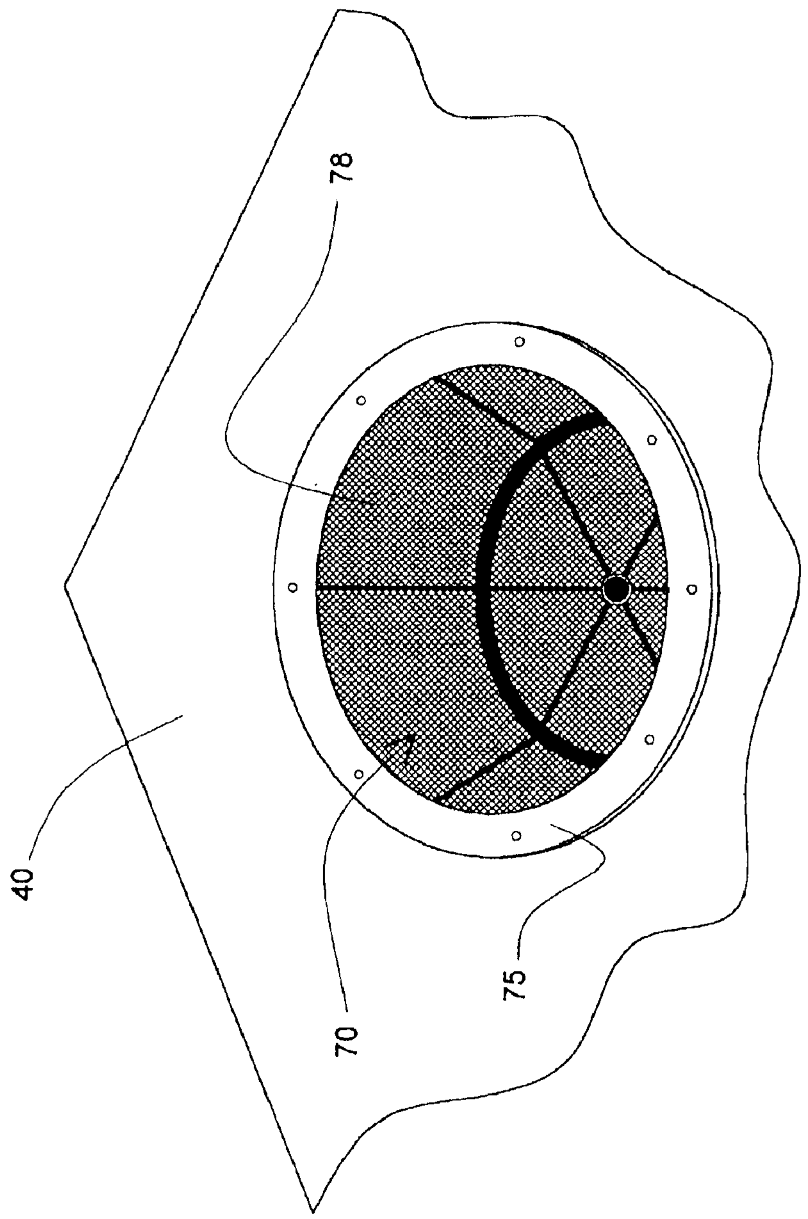
FIG. 3 is a partial, perspective view of the particulate means mounted in the cover of the liquid receptacle.

Suspended within liquid receptacle 20 is particulate means 70 for receiving a selected amount of particulate matter. The particulate means 70 is sized to receive the appropriate amount of particulate matter so that when the aeration process is complete, the concentration of beneficial organisms suspended in the liquid is at a desired level, as would be known by one of ordinary skill in the art. FIG. 3 depicts particulate means 70, and flange 75 to enable the particulate means 70 to be installed in lid 40. In this exemplary embodiment, particulate means 70 is molded cylindrical plastic basket with meshed side walls and bottom, the orifices of the mesh sized to retain the particulate matter until being dislodged from means 70 by aeration. The geometric shape of particulate means 70 is not a limitation of the invention. It is only necessary that the geometry enable the aeration effects to separate the beneficial organisms from the particulate matter. The baskets design permit the particulate means 70 to be easily removed for easy cleaning between cycles. Flange means 75 may be recessed into lid 40 or may protrude slightly above the surface of lid 40, in which case flange 75 may be threaded on its outer perimeter to receive complementarily thread cover 45 (FIG. 1).

Figure 2:
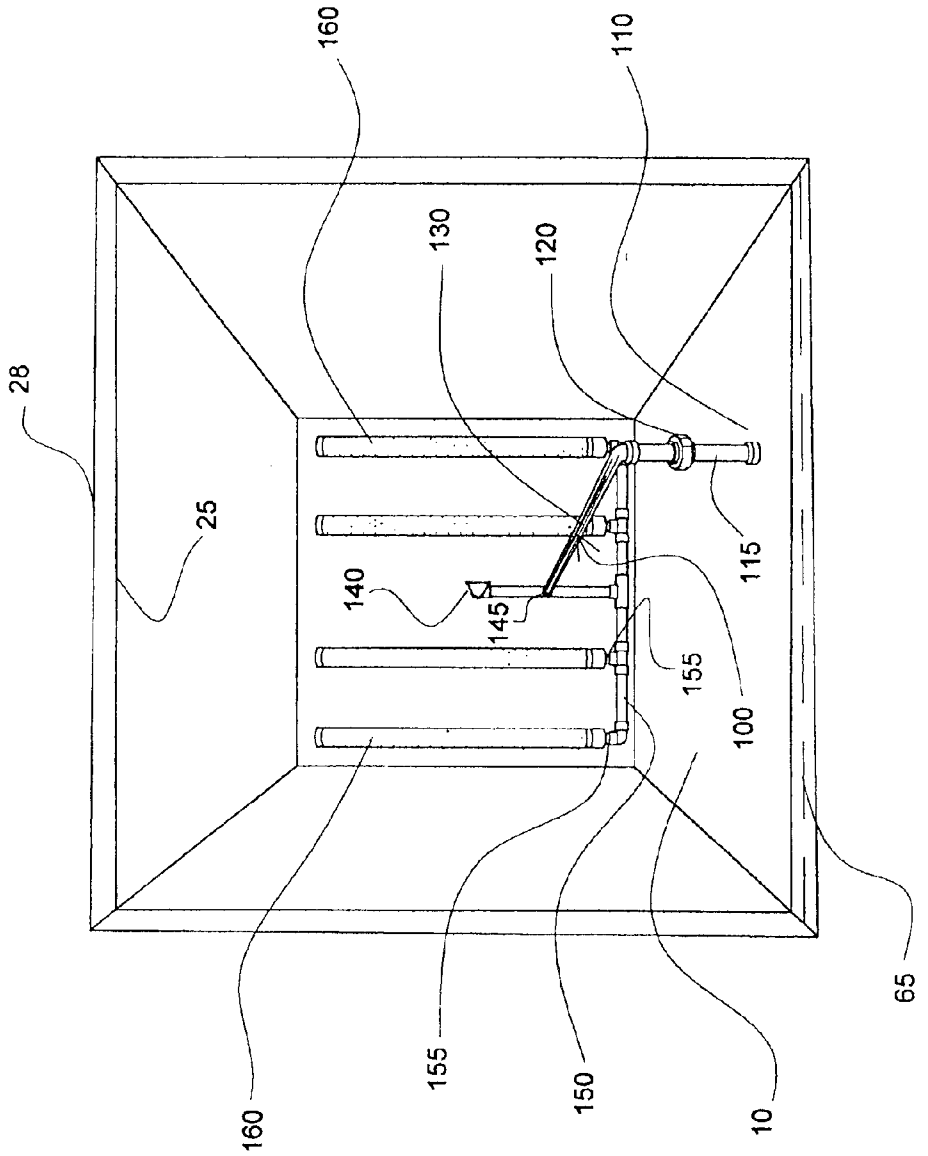
FIG. 2 is a plan view of the apparatus of liquid receptacle containing the aerating means of the invention.
Figure 4:
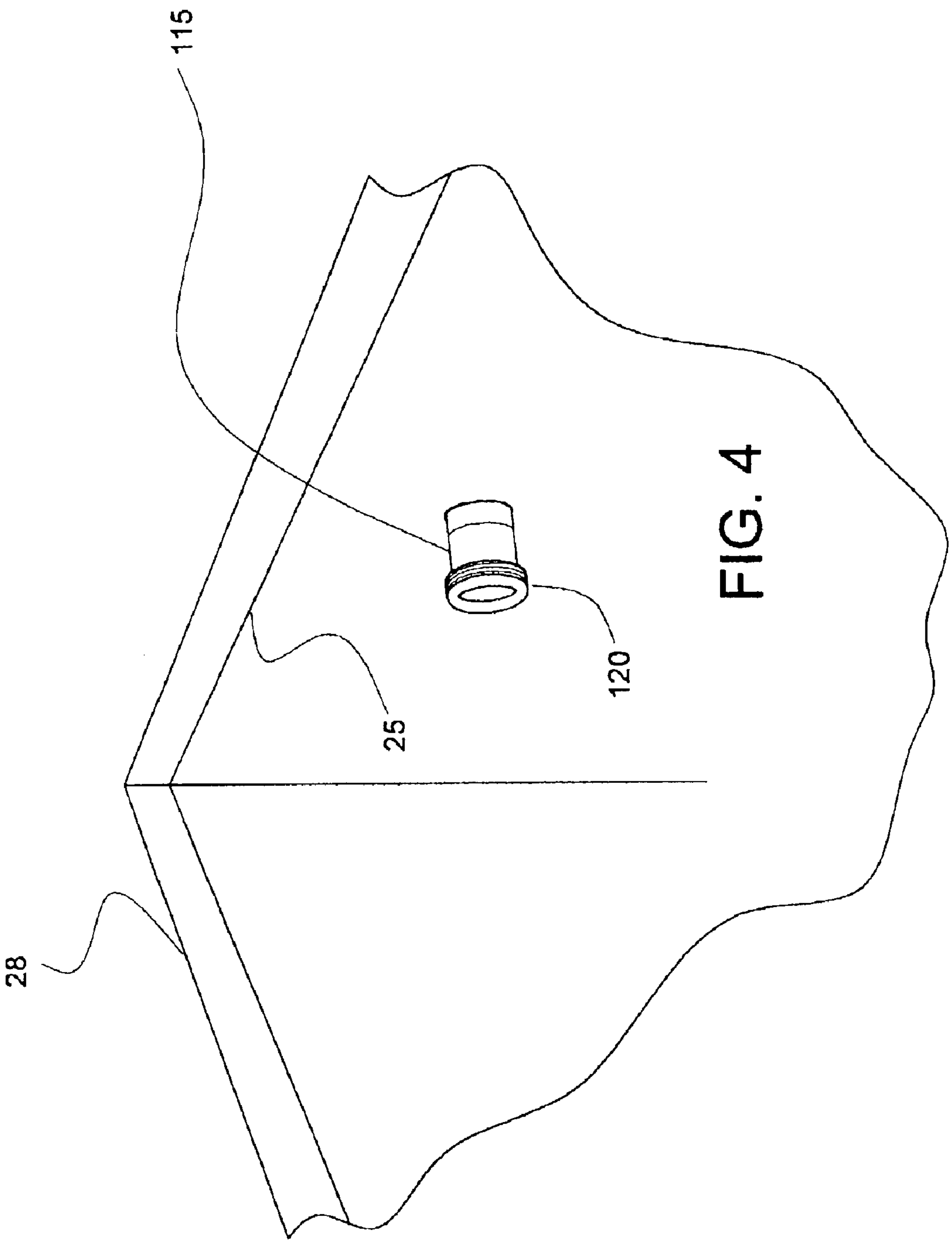

Aeration means 100 is shown in FIG. 2, which is a plan view of the inner surfaces of liquid receptacle 20. Aeration means 100 consists of an inlet 110, which is preferrable located adjacent the top rim of the inner surface of liquid receptacle 20 (FIG. 4), and which communicates air from blower 50 to the diffusers 140 and 160. In the event that inlet 110 is located at or near the bottom of liquid receptacle 20, then inlet 110 would also require valving to inhibit liquid in the receptacle from back flow into tile blower. Inlet 110 includes a duct, which in this exemplar embodiment is shown as through pipe 115, which extends through liquid receptacle 20 to the outlet of blower 50 (not shown), and a quick disconnect coupler 120 that complementarily couples with transmission coupler 130, that is intermediate to inlet 110 and manifold 150. Quick disconnect couplers are well known to those of ordinary skill of the are, and it is well within the skill of the art to devise the plumbing system for the diffusers and manifold. Manifold 150 is sized to distribute air to a selected number of diffusers. In this exemplary embodiment, the manifold is formed of polyvinyl chloride (PVC). PVC provides light weight for ease of removal and re-assembly, greatly reduces the possibility of scraping the side walls which will damage the tank, provides easy to clean surfaces, provides constant positioning of the duckbill and tubular diffusers and more importantly, provides an inert surface to prevent contamination of microorganisms. The PVC manifold enables an entire diffuser unit removable between cycles for cleaning.

The number of diffusers is determined by the inner bottom surface area of liquid receptacle 20. As shown in this exemplary embodiment, manifold 150 is in the shape of an inverted T, having a selected number of nipples 155 to complimentarily mate with distribution diffusers 160. The base leg 145 of the T complementarily mates with duck-billed coarse diffuser 140. Duck-billed coarse diffuser 140 is situated in liquid receptacle 20 so that it aerates the bottom side of particulate means 70, such that when particulate matter is in the particulate means 70, liquid receptacle 20 filled with liquid such that water saturates the particulate matter, and air passes through manifold 150, coarse diffuser 140 is used to provide a specific volume of air (10 cubic feet per minute (cfm) of air in 26–30 inches of water) to hit the bottom of particulate means 70 and disperse air in all directions. This obtains the bubble mechanical force needed to dislodge the beneficial microorganisms from the particulate matter without destroying or smashing the microorganisms. In this exemplary embodiment, duckbill diffusers have been employed because they provide vigorous turbulence to extract organisms from the particulate matter, they provide mixing agitation, they can be plumbed into position directly beneath each basket to hit the particulate matter with the strongest force. In addition, they eliminate the need for circulating pumps that would destroy microorganism by impellers. However, the choice of diffusers is a matter of design choice, and the use of pumps would not be barred if their use would not neutralize the beneficial organisms.

Distribution diffusers 160 extend perpendicular to the cross portion of the T, and are parallel to and adjacent the Rat bottom of liquid receptacle 20. Distribution diffusers 160 are sized to cover a substantial portion of the surface area of the bottom so that they maintain the particulate matter in suspension until a maximum number of beneficial organisms are separated out and absorbed by the liquid, thereby constituting the foliar liquid. In this exemplary embodiment, distribution diffusers 160 are fine, tubular diffusers, providing 2.5 cfm of air per diffuser. Tubular diffusers provide large quantities of dissolved oxygen for maximum biological organism growth, sustain the suspension of the beneficial organisms in the "tea," and maintain constant dissolved oxygen levels for aerobic conditions. One of ordinary skill in the art would realize that not all of the beneficial organisms will be absorbed in the liquid, and that not all of the particulate matter can be separated, however, the diffuser configuration and aeration of the bottom of the tank will maintain the particulate matter in suspension throughout the aeration process to maximize absorption, after which, some of the beneficial organisms and particulate matter will drop to the bottom surface of liquid receptacle 20. The diffusers are known to those of ordinary skill in the art, and are described in U.S. Pat. No. 6,016,839, "Tideflex Coarse Bubble Diffuser, and U.S. Pat. No. 6,193,220, "Combination Fine & Coarse Bubble Aeration System," both of which are assigned to Red Valve Company, Inc. However, other diffusers may be selected as a matter of design choice.

In this exemplary embodiment, a 30 cfm regenerative blower 50 is used to inject air into manifold 150. Since aeration means 100 is connected to inlet 110 by quick disconnect coupler 120, the complete manifold transmission and distribution system may be removed from liquid receptacle 20, permitting easy access to tile interior of liquid receptacle 20 for cleaning. Thus the manifold transmission and distribution system may be separated and cleaned, ensuring that there is no opportunity for growth of anti-microbial matter that would inhibit the beneficial organisms. With the manifold removed, liquid receptacle 20 is easily flushed out, and contaminants are easily removed from the smooth, accessible surfaces of liquid receptacle 20.

Recent studies have shown that maintaining the selected liquid in a preferred temperature range optimizes absorption of the beneficial organisms and microbial growth conditions for the beneficial organisms. Such preferred temperature range is 65° F.–70° F. Thus liquid receptacle 20 is of double wall, plastic construction, having inner wall 25 and outer wall 28 (FIG. 4), which permits insulation of the selected liquid from ambient temperatures and conditions. It should be noted that although the exemplary embodiment includes double wall construction, such is not a limitation of the invention, and one of ordinary skill in the art would know of methods of maintaining a single wall receptacle within the appropriate temperature range. Control means 60 functions to keep the selected liquid at the selected temperature by means of heating and/or cooling coils 65 located between the double walls of liquid receptacle 20. Heating and cooling systems are well known to one of ordinary skill in thee art, and are only a matter of design choice. An example of cooling means would be standard refrigeration cooling coils. Control means 60 includes circuitry for controlling the duration of the operation cycle of the aerators and temperature control circuitry.

The inner surface of inner wall 25 is preferably constructed of a smooth non-porous, slick fiberglass material to limit the adhesion of tea biofilm, with the interior corners 225 (FIG. 5) rounded, to enable easy cleaning of the surfaces, basically a horizontal, rectangular bathtub design. Thus, there are no nooks and crannies where anti-microbial conditions can exist, or anaerobic conditions occur. Tap drain 35 is provided to express the foliar liquid from liquid receptacle 20. Tap drain 35 provides a flow path for the foliar liquid from a point adjacent the upper surface of diffusers 160 to a selected point on the base to enable the expressing of the foliar spray from liquid receptacle 20. An exhaust drain 38 provides a flow path to express waste and cleaning materials from receptacle 20 once the foliar liquid has been removed. Exhaust drain 38 communicates with the bottom interior surface of receptacle 20 so that all particulate matter not absorbed in the foliar liquid may be easily removed from receptacle 20 by flushing, or equivalent means. Although fiberglass is the selected material for construction of liquid receptacle 20, other materials may be employed that have the characteristics of a low-porous/non-porous surface, to limit the adhesion of the tea biofilm; a slick surface that allows ease of cleaning, high strength and a durable finish for long life. Also beneficial is a totally opaque material that blocks out ultraviolet light. Also of consideration is the capacity to construct a heating/cooling unit 90 into the base of the receptacle with heating/cooling coils 65 distributed through the double-walled sides of the liquid receptacle.

Lid 40 is constructed of a plastic material, and molded to include an orifice for receiving particulate means 70 (FIG. 3). Removably attached to lid 40 is cover 45, which cover 45 includes a gasket on its bottom surface to insulate and isolate the particulate means from ambient conditions. In this exemplary embodiment cover 45 is of "screw cap" type to enable the liquid receptacle to be sealed. Cover 45 is also contains the foam created by aeration during brewing cycle. This design enables cover 45 to be easily removed for access and disassembly for cleaning.

Referring again to FIG. 1, liquid receptacle 20 is mounted on base 30, which elevates receptacle 20 to a height to permit expressing of the foliar liquid from receptacle 20. Base 30 also serves as a platform for cleaning the interior of liquid receptacle 20. In FIG. 1, tap drain 35 and exhaust drain 38 extend through base 30 for easy access. In other embodiments, tap drain 35 and exhaust drain 38 may extend directly from and adjacent to bottom of liquid receptacle 20.

Referring now to FIG. 5, depicted is a schematic of an extended manifold system for use in a larger liquid receptacle. As can readily be seen, the amount of foliar liquid that may be produced is not limited by the apparatus of the invention. In this embodiment, the five hundred gallon liquid receptacle would have the same height and width as the one-hundred gallon receptacle of FIG. 1, but would have a longer length. Correspondingly, efficient operation of the apparatus would require an additional number of particulate means, coarse diffusers, and tubular diffusers. Not shown in aeration means 200 of FIG. 5 are the inlet means 110, which may consist on one single inlet, or a plurality of inlets. It is only necessary that the blower means provide an equivalent amount of airflow to each of the coarse diffusers and tubular diffusers as noted above. The exemplary embodiment of FIG. 5 depicts the bottom surface 215 of the liquid receptacle, having rounded corner 205, and two manifold systems 210 and 220. Not shown is the equivalent through pipe 115, quick disconnect coupler 120 and the transmission coupler 130, that is intermediate between inlet 110 and manifolds 210 and 220. Manifolds 210 and 220 are sized to distribute air to a selected number of diffusers. As with the diffuser system of FIG. 2, the number of diffusers is determined by the inner bottom surface area of the liquid receptacle. In the case of the 500-gallon liquid receptacle, the width of the receptacle is 40 inches, and its length is 106 inches. FIG. 5 shows a manifold system wherein there are 4 duck-billed coarse diffusers 240 and 8 tubular distribution diffusers 260. Thus it is obvious that size of the liquid receptacle is not a limitation of the invention. The size of the receptacle is only limited by the capacity of the aeration system to provide sufficient air at the diffusers to break up the particulate matter, and release the beneficial organisms into the liquid.

While the present description contain many specificities, these should not be construed as limitations on the scope of the invention, but rather as an exemplification of some preferred embodiments thereof. For example, it would be well within the skill of the art to incorporate a water purification system by industrial quality reverse osmosis prior to the intake valve. Such a system would provide a high level of water purification to remove salts, chlorine, and other materials that are harmful to the production of quality tea. Such a system would also provide for preliminary water testing and pretreatment of water dependent upon conditions, and provide a consistent quality water for the aeration process. Additionally, it would be obvious to include an exterior thermostat, located on the side of the tank in a waterproof housing, for temperature control. Accordingly, the scope of the invention should not be determined by the specific embodiments illustrated herein, but rather in light of the full scope of the claims appended hereto.

We claim:

1. An apparatus for making a foiliar liquid, the apparatus comprising:

(a) a non-porous liquid receptacle for receiving a selected amount of liquid;

(b) at least one particulate means for receiving a selected amount of particulate matter having beneficial micro-organisms;

(c) air supply means for supplying a constant flow of air to an aerating means;

(d) the aerating means, incorporated within the receptacle, for aerating the liquid and the particulate matter, the aerating means being selectively proportionate to the volume of the receptacle, the aerating means having means for communicating with the air supply means;

(e) a lid for isolating the receptacle for receiving the selected amount of liquid from ambient conditions, the lid including flange means for receiving the particulate means; and wherein, when the selected amount of liquid is placed in the liquid receptacle, a selected amount of particulate matter having beneficial organisms is placed in the particulate means, and when air is diffused through the liquid receptacle and the particulate matter, the micro-organisms are separated from the particulate material in a manner to be suspended in the liquid.

2. The apparatus of claim 1 wherein the liquid receptacle is fabricated from a fiberglass material.

3. The apparatus of claim 1 wherein the liquid receptacle is a substantially horizontal rectangular tank having a flat bottom and an upper surface, the liquid receptacle having an intake means and an outlet means, the intake means for receiving air to the aerating means, the outlet means for expressing the foliar liquid from the receptacle.

4. The apparatus of claim 3 wherein the intake means is a duct for transporting air from a means for supplying air, the duct having means for communicating with the means for aerating the liquid.

5. The apparatus of claim 3 wherein the duct having means for communicating with the means for aerating the liquid includes a quick-disconnect coupler.

6. The apparatus of claim 1 wherein the means for supplying air is a blower located adjacent the exterior of the receptacle.

7. The apparatus of claim 3 wherein the outlet means includes a valve to control the flow of the liquid.

8. The apparatus of claim 1 wherein the particulate means is a perforated receptacle, the perforated receptacle sized to fit within the liquid receptacle.

9. The apparatus of claim 8 wherein perforated receptacle is a basket, supported adjacent the upper surface of the liquid receptacle.

10. The apparatus of claim 9 wherein the basket is cylindrical.

11. The apparatus of claim 9 wherein the basket is fabricated from a plastic material.

12. The apparatus of claim 1 wherein the aerating means includes an air diffuser located adjacent the bottom of the liquid receptacle.

13. The apparatus of claim 12 wherein the diffuser comprises a manifold with a selected number of diffuser arms, the number of diffuser arms selected to cover a substantial portion of the area of the bottom surface of the liquid receptacle.

14. The apparatus of claim 13 wherein the manifold includes a quick-disconnect coupler for connecting with the inlet means.

15. The apparatus of claim 1 additionally including cover means for isolating the particulate means from ambient temperature.

16. The apparatus of claim 1 additionally including temperature control means for maintaining the temperature within the liquid receptacle at a selected level.

17. She apparatus of claim 1 additionally including a base for supporting the liquid receptacle.

18. The apparatus of claim 2 additionally including a drain for expressing excess residue from the liquid receptacle.

19. The apparatus of claim 18 wherein the drain includes a valve to control the flow of the excess particulate matter.

20. An apparatus for making a foliar liquid, the apparatus comprising:

(a) a non-porous liquid receptacle for receiving a selected amount of liquid, the liquid receptacle comprising a substantially horizontal, rectangular tank having a flat bottom and an upper surface, the liquid receptacle having:

(i) an intake means, the intake means for receiving air to the aerating means, (ii) an outlet means, the outlet means for expressing the foliar liquid from the receptacle, (iii) a drain for expressing excess particulate matter from the liquid receptacle;

(b) at least one perforated receptacle for receiving a selected amount of particulate matter having beneficial micro-organisms, the perforated receptacle sized to fit within the liquid receptacle;

(c) air supply means for supplying a constant flow of air to an aerating means;

(d) the aerating means, incorporated within the receptacle, for aerating the liquid and the particulate matter, the aerating means being selectively proportionate to the volume of the receptacle, the aerating means including an air diffuser located adjacent the bottom of the liquid receptacle, the aerating means having means for communicating with the intake means;

(e) a lid, the lid for isolating the liquid receptacle from ambient conditions, the lid including flange means for receiving the particulate means;

(f) temperature control means for maintaining the temperature within the liquid receptacle at a selected level;

(g) including a base for supporting the liquid receptacle; and wherein, when the selected amount of liquid is placed in the liquid receptacle, a selected amount of particulate matter having beneficial organisms is placed in the particulate means, and when air is diffused through the liquid receptacle and the particulate matter, the micro-organisms are separated from the particulate material in a manner to be suspended in the liquid.

21. The apparatus of claim 20 wherein the liquid receptacle is fabricated from a fiberglass material.

22. The apparatus of claim 20 wherein the intake means is a duct for transporting air from a means for supplying air, the duct having means for communicating with the means for aerating the liquid.

23. The apparatus of claim 22 wherein the duct having means for communicating with the means for aerating the liquid includes a quick-disconnect coupler.

24. The apparatus of claim 20 wherein the means for supplying air is a blower located adjacent the exterior of the receptacle.

25. The apparatus of claim 20 wherein the outlet means includes a valve to control the flow of the liquid.

26. The apparatus of claim 20 wherein perforated receptacle is a basket, supported adjacent the upper surface of the liquid receptacle.

27. The apparatus of claim 26 wherein the basket is cylindrical.

28. The apparatus of claim 26 wherein the basket is fabricated from a plastic material.

29. The apparatus of claim 20 wherein the diffuser comprises a manifold with a selected number of diffuser arms, the number of diffuser arms selected to cover a substantial portion of the area of the bottom surface of the liquid receptacle.

30. The apparatus of claim 29 wherein the manifold includes a quick-disconnect coupler for connecting with the inlet means.

31. The apparatus of claim 20 additionally including cover means for isolating the particulate means from ambient temperature.

32. An apparatus for making a foliar liquid, the apparatus comprising:

(a) a non-porous liquid receptacle for receiving a selected amount of liquid, the liquid receptacle comprising a substantially horizontal, rectangular tank having a flat bottom and an upper surface, the liquid receptacle having:

(i) an intake means, the intake means for transporting air from a blower to a manifold means, the intake means comprising a duct and a quick-disconnect coupler for communicating with the manifold means;

(ii) an outlet means, the outlet means for expressing the foliar liquid from the receptacle, the outlet means including a valve to control the flow of the liquid, (iii) a drain for expressing excess particulate matter from the liquid receptacle, the drain including a valve to control the flow of the excess particulate matter;

(b) at least one cylindrical basket, supported adjacent the upper surface of the liquid receptacle, the at least one basket for receiving a selected amount of particulate matter having beneficial micro-organisms, the at least one basket sized to fit within the liquid receptacle;

(c) a blower for supplying a constant flow of air to an aerating means, the blower located adjacent the exterior of the receptacle;

(d) the manifold means, incorporated within the receptacle, for aerating the liquid and the particulate matter, the manifold means being selectively proportionate to the volume of the receptacle, the manifold means including a manifold with a selected number of diffuser arms, the number of diffuser arms selected to cover a substantial portion of the area of the bottom surface of the liquid receptacle, the manifold means having means for communicating with the intake means;

(e) a lid, the lid for isolating the liquid receptacle from ambient conditions, the lid including flange means for receiving the particulate means;

(f) a cover for isolating the particulate means from ambient temperature;

(g) temperature control means for maintaining the temperature within the liquid receptacle at a selected level;

(h) including a base for supporting the liquid receptacle; and wherein, when the selected amount of liquid is placed in the liquid receptacle, a selected amount of particulate matter having beneficial organisms is placed in the particulate means, and when air is diffused through the liquid receptacle and the particulate matter, the microorganisms are separated from the particulate material in a manner to be suspended in the liquid.

33. The apparatus of claim 32 wherein the liquid receptacle is fabricated from a fiberglass material.

34. The apparatus of claim 32 wherein the basket is fabricated from a plastic material.

35. The apparatus of claim 32 wherein the manifold includes a quick-disconnect coupler for connecting with the inlet means.

* * * * *